US00PP21173P2

(12) United States Plant Patent
Lewis et al.

(10) Patent No.: US PP21,173 P2
(45) Date of Patent: Jul. 20, 2010

(54) ***CAMPANULA* PLANT NAMED 'PINKINS'**

(50) Latin Name: *Campanula poscharskyana*
Varietal Denomination: Pinkins

(75) Inventors: Peter Lewis, Cambridge (GB); Susan Lewis, Cambridge (GB)

(73) Assignee: Sue Wooster, Diss, Norfolk (GB)

( * ) Notice: Subject to any disclaimer, the term of this patent is extended or adjusted under 35 U.S.C. 154(b) by 0 days.

(21) Appl. No.: 12/455,005

(22) Filed: May 27, 2009

(51) Int. Cl.
*A01H 5/00* (2006.01)

(52) U.S. Cl. ..... Plt./414
(58) Field of Classification Search ..... Plt./263, Plt./414
See application file for complete search history.

*Primary Examiner*—Susan B McCormick Ewoldt
(74) *Attorney, Agent, or Firm*—Penny J. Aguirre

(57) ABSTRACT

A new cultivar of *Campanula*, 'Pinkins', characterized by its flowers that are deep lilac pink in color with lighter colored centers, its refined foliage that is rich green in color with reddish purple highlights under intense light conditions, its moderate and less invasive growth habit than is typical for this type of *Campanula*, and its cold hardiness in U.S.D.A. Zone 3.

2 Drawing Sheets

Botanical classification: *Campanula poscharskyana.*
Cultivar designation: 'Pinkins'.

BACKGROUND OF THE INVENTION

The present invention relates to a new and distinct cultivar of *Campanula* plant, botanically known as *Campanula poscharskyana* 'Pinkins' and will be referred to hereafter by its cultivar name, 'Pinkins'. The new cultivar represents a new Bellflower, an herbaceous perennial grown for landscape use in garden borders, raised beds, rock gardens and containers.

The Inventor discovered the new cultivar, 'Pinkins', in a garden at their nursery in West Wratting, Cambridgeshire, England in 1992. 'Pinkins' originated as a naturally occurring lilac-pink flowered basal shoot mutation found on an unnamed blue flowering plant of *Campanula poscharskyana.*

Asexual reproduction of the new cultivar was first accomplished by division in West Wratting, U.K. in 1992 by one of the Inventors. Propagation by basal stem cuttings and division has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Pinkins' from other varieties of *Campanula* known to the inventor.

1. 'Pinkins' exhibits distinct flowers that are deep lilac-pink in color with lighter colored centers.
2. 'Pinkins' exhibits refined foliage that is rich green in color with reddish purple highlights under intense light conditions.
3. 'Pinkins' exhibits a moderate, less invasive growth habit than is typical for the species.
4. 'Pinkins' is cold hardy to U.S.D.A. Zone 3.

'Pinkins' differs from its parent variety by having flowers that are deep lilac pink in color rather than blue, in having foliage that is more refined and richer green in color, and in having a more moderate growth habit. The new cultivar is most similar in plant habit and flower form to the cultivars 'Lisduggen Variety' (unpatented), and 'Lilacina' (unpatented), both selections of *Campanula poscharskyana*. 'Pinkins' differs from the two comparison cultivars by having flowers that are more pink in color, in having foliage that is less coarse, and in having a less invasive growth habit.

BRIEF DESCRIPTION OF THE DRAWING

The accompanying colored photographs illustrate the overall appearance and distinct characteristics of the new *Campanula*. The photographs were taken in September 2007 of a one year-old plant as grown in a 15 cm container in Cambridgeshire, England.

The photograph in FIG. 1 is a side view of a plant of 'Pinkins' in bloom.

Figure 1:
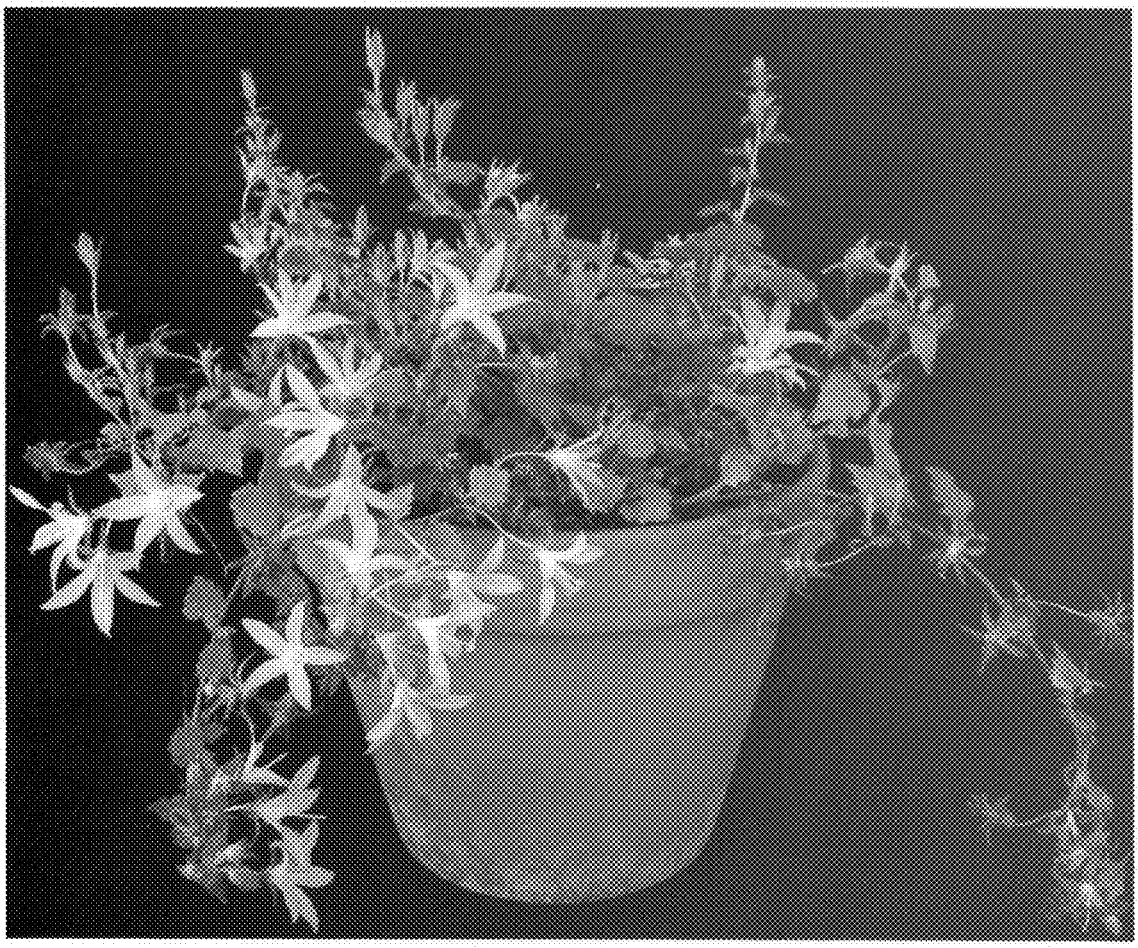
Figure 2:
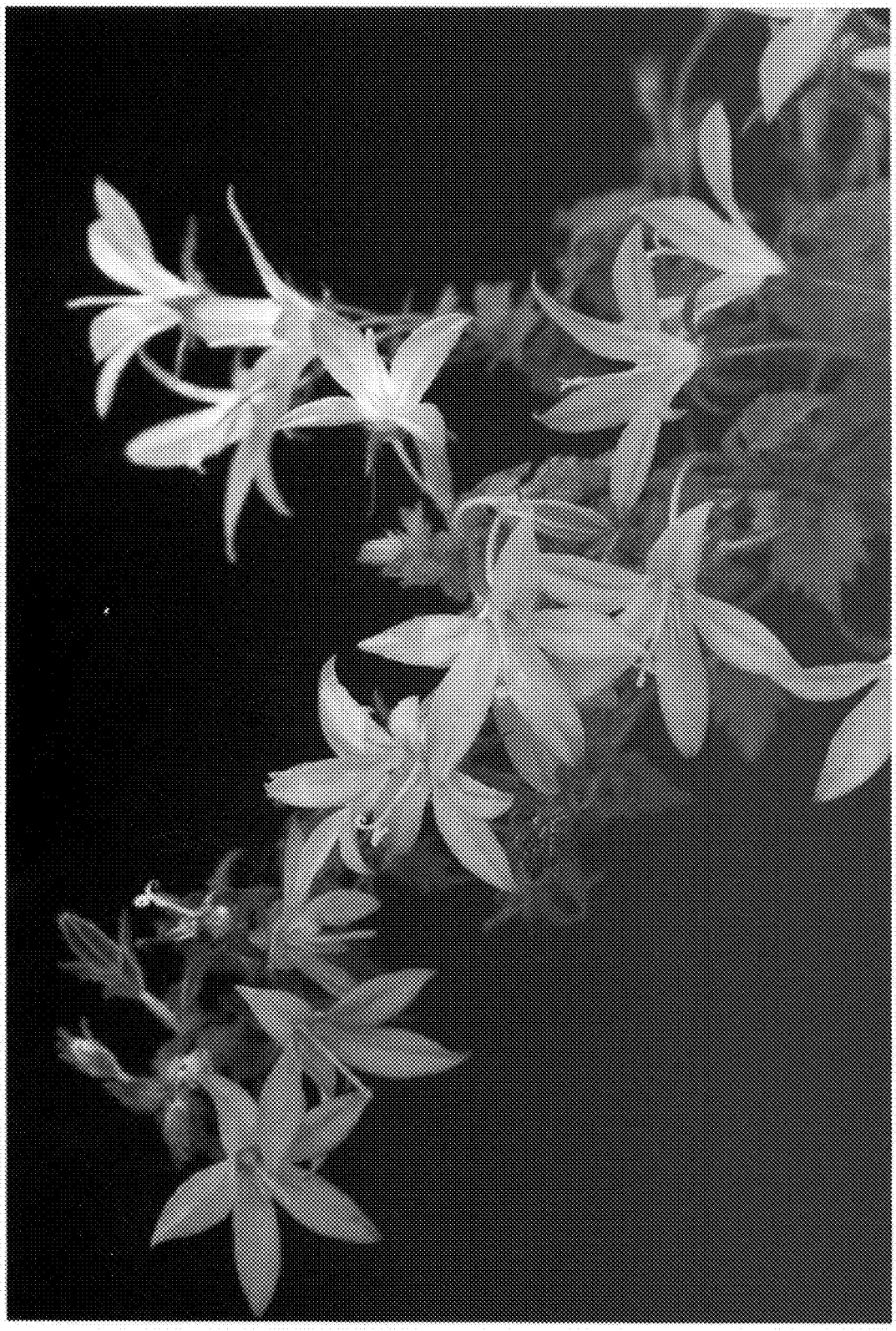

The photograph in FIG. 2 is a close-up view of the flowers of 'Pinkins'.

The colors in the photographs may differ slightly from the color values cited in the detailed botanical description, which accurately describe the colors of the new *Campanula.*

DETAILED BOTANICAL DESCRIPTION OF THE PLANT

The following is a detailed description of a one year-old plant of the new cultivar as grown outdoors in a 15 cm container in Cambridgeshire, U.K. under natural lighting with average temperatures of 12° C. to 25° C. (day) and 4° C. to 14° C. (night). The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

*Plant type.*—Herbaceous semi-evergreen perennial.

*Blooming period.*—Mid May to October and possibly into December in the U.K. depending on weather conditions.

*Plant habit.*—Low growing, trailing habit with inflorescences initially upright then arching downward from weight of the number of open flowers.

*Height and spread.*—Reaches about 150 mm in height and about 500 mm in spread.

*Cold hardiness.*—USDA Zone 3.

*Heat tolerance.*—At least tolerant to 30° C.

*Diseases and pests.*—No susceptibility or resistance to diseases or pests has been observed.

*Root description.*—Fine, fibrous.

Growth and propagation:

*Growth rate.*—Moderately vigorous, less vigorous than the species and observed cultivars of Campanula poscharskyana.

*Propagation.*—Division of the lateral rosettes or basal stem cuttings.

*Time required for to finish crop.*—Cropping time from a rooted liner about 4 to 6 weeks to fully develop in a 7 cm container.

Stem description:

*Stem size.*—Average of 20 cm in length (excluding inflorescence) and 2 mm in width.

*Stem shape.*—Round.

*Stem color.*—144B.

*Stem surface.*—Eglandular pubescent.

*Internode length.*—About 2 cm.

*Branching habit.*—Flowering stems branch freely from the basal foliage, at about a 30° angle.

Foliage description:

*Leaf shape.*—Cordate.

*Leaf division.*—Simple.

*Leaf base.*—Cordate.

*Leaf apex.*—Acute.

*Leaf venation.*—Pinnate, barely visible on upper surface, closest to 139D in color on lower surface.

*Leaf margins.*—Serrate, undulate.

*Leaf attachment.*—Petiolate.

*Leaf petiole.*—About 2.5 cm in length and 1 mm in width, 143C in color, surface eglandular and pubescent, stipules absent.

*Leaf arrangement.*—Alternate.

*Leaf surface.*—Finely pubescent on upper surface, sparsely pubescent on veins of lower surface.

*Leaf color.*—Upper surface 137C, lower surface 137C.

*Leaf size.*—Average of 2 cm in length and 1.5 cm in width.

*Leaf quantity.*—Average of 14 per branch.

*Leaf fragrance.*—None observed.

Flower description:

*Inflorescence type.*—Loose panicle.

*Inflorescence size.*—Up to 1.1 cm in length and 7 cm in width.

*Flower fragrance.*—None.

*Flower number.*—Average of 25 per inflorescence, one inflorescence per stem.

*Lastingness of flower.*—About 10 days, persistent.

*Flower aspect.*—Upright to horizontal, dependant on location of the inflorescence.

*Flower bud.*—An average of 1.3 cm in length and up to 4 mm in width, oblong in shape, 83C in color.

*Flower form.*—Campanulate.

*Flower size.*—Average of 7.5 cm in depth and 3.9 cm in width.

*Corolla form.*—Petals open nearly funnel formed maturing to near explanate with lower potion fused into tube.

*Petals.*—5, free portion; an average of 1.2 cm in length and 5 mm in width, ensiform-elliptic in shape and weakly recurved, entire margin, acute apex, upper surface close to 76C in color, lower surface close to 76A, surface smooth on both surfaces, tube; about 4 mm in length and 4 mm in width, close to 76D in color.

*Calyx.*—Rotate in shape, an average of 1.5 cm in wide and 4 mm in height.

*Sepals.*—5. lanceolate in shape and weakly reflexed, entire and slightly ciliate margin, average of 8 mm in length and 2 mm in width, finely pubescent surface, acute apex, cuneate and fused base, color of upper and lower surface is 139D at the base and strongly tinged with N187B toward the upper half.

*Peduncle.*—No clearly defined peduncle below lowest flower, up to 100 mm within the inflorescence and 1.5 mm in diameter, slightly arching in aspect, round in shape, pubescent surface, color is close to N187B in sun and 144B in shade.

*Pedicels.*—Average of 22 mm in length and less than 1 mm in width, round in shape, slightly arching in aspect, pubescent surface, 144D n color.

Reproductive organs:

*Gynoecium.*—1 pistil, stigma is trifid in shape with strongly recurved tips, about 2 mm in length and 0.5 mm in width and 76C in color intensifying at the tips of the lobes, style is cylindrical in shape, about 1 cm in length, less than 1 mm in width and 76C in color at the apex fading to 155C at the base, ovary is inferior, 1.5 mm in length and 2 mm in width, rounded-conical in shape, deeply furrowed, pubescent, and 143C in color.

*Androcoecium.*—5 stamens, anthers are basifixed, thread-like in shape, about 3 mm in length, less than 0.5 mm in width and 2D in color, filament is about 3 mm in length, 155C in color, pollen is low in abundance and insufficient in quantity to color code.

*Seeds.*—About 20 per capsule, ovoid in shape, about 0.8 mm in length and 0.5 mm in width and 175A in color.

It is claimed:

1. A new and distinct cultivar of *Campanula* plant named 'Pinkins' as herein illustrated and described.

* * * * *